United States Patent
Pirzada et al.

(10) Patent No.: US 11,491,256 B2
(45) Date of Patent: Nov. 8, 2022

(54) SYSTEM AND METHOD FOR TREATING A WOUND

(71) Applicant: GENADYNE BIOTECHNOLOGIES, INC., Hicksville, NY (US)

(72) Inventors: Shahzad Saad Pirzada, Old Westbury, NY (US); Chien Ming Goh, Great Neck, NY (US)

(73) Assignee: GENADYNE BIOTECHNOLOGIES, INC., Hicksville, NY (US)

( * ) Notice: Subject to any disclaimer, the term of this patent is extended or adjusted under 35 U.S.C. 154(b) by 0 days.

(21) Appl. No.: 16/285,945

(22) Filed: Feb. 26, 2019

(65) Prior Publication Data
US 2019/0192729 A1  Jun. 27, 2019

Related U.S. Application Data

(62) Division of application No. 15/419,965, filed on Jan. 30, 2017, now abandoned.
(Continued)

(51) Int. Cl.
A61L 26/00 (2006.01)
A61L 15/28 (2006.01)
A61L 15/40 (2006.01)

(52) U.S. Cl.
CPC .......... *A61L 26/0066* (2013.01); *A61L 15/28* (2013.01); *A61L 15/40* (2013.01); *A61L 26/0004* (2013.01);
(Continued)

(58) Field of Classification Search
None
See application file for complete search history.

(56) References Cited

U.S. PATENT DOCUMENTS

| | | | |
|---|---|---|---|
| 4,600,711 A | | 7/1986 | Swerczek |
| 4,608,044 A | * | 8/1986 | Nordqvist ............... A61L 15/18 424/447 |

(Continued)

FOREIGN PATENT DOCUMENTS

| | | | | |
|---|---|---|---|---|
| CN | 102552965 | * | 7/2012 | ............... A61K 8/02 |
| CN | 103418018 A | | 12/2013 | |

(Continued)

OTHER PUBLICATIONS

English Translation of—Hong, Feng, CN 102552965, published Jul. 11, 2012, pp. 1-36 (Year: 2012).*
(Continued)

*Primary Examiner* — Aradhana Sasan
(74) *Attorney, Agent, or Firm* — Collard & Roe, P.C.

(57) ABSTRACT

In at least one embodiment there is a wound application comprising at least one film applied over a wound comprising at least 1% green tea, and at least 0.01% sugar, wherein said film comprises a polymeric film comprising united chains and monomeric glucose points. In at least one other embodiment there is a wound application comprising a solution comprising at least trace amounts of colloidal silver, at least trace amounts of sodium chloride, at least trace amounts of dextrose; and water, wherein the colloidal silver, the sodium chloride and the dextrose are dissolved in water. In at least one other embodiment there is an application for treating a wound comprising both a solution comprising at least trace amounts of colloidal silver and a film comprising at least trace amounts of green tea applied over the solution on top of a wound.

11 Claims, 11 Drawing Sheets

Related U.S. Application Data

(60) Provisional application No. 62/288,612, filed on Jan. 29, 2016.

(52) U.S. Cl.
CPC ..... *A61L 26/0057* (2013.01); *A61L 2300/104* (2013.01); *A61L 2300/404* (2013.01); *A61L 2300/406* (2013.01)

(56) References Cited

U.S. PATENT DOCUMENTS

| | | | | |
|---|---|---|---|---|
| 4,929,550 | A | * | 5/1990 | Byrom .................... C12P 19/04 |
| | | | | 435/101 |
| 5,116,620 | A | * | 5/1992 | Chvapil .................. A61L 15/18 |
| | | | | 424/443 |
| 5,133,965 | A | * | 7/1992 | Fountain ................ A01N 25/04 |
| | | | | 424/405 |
| 5,785,972 | A | * | 7/1998 | Tyler ...................... A61K 36/28 |
| | | | | 424/539 |
| 5,846,213 | A | * | 12/1998 | Wan .................. A61F 13/00012 |
| | | | | 602/49 |
| 6,696,077 | B2 | | 2/2004 | Scherr |
| 6,753,454 | B1 | | 6/2004 | Smith et al. |
| 2006/0046970 | A1 | | 3/2006 | Bowman et al. |
| 2014/0163447 | A1 | * | 6/2014 | Wieland ................ A61L 15/325 |
| | | | | 602/47 |
| 2015/0238648 | A1 | | 8/2015 | Matouk |

FOREIGN PATENT DOCUMENTS

| | | | | | |
|---|---|---|---|---|---|
| CN | 104814982 | A | | 8/2015 | |
| DE | 202009014065 | U1 | | 2/2010 | |
| EP | 1764104 | A1 | * | 3/2007 | ............. A61K 31/07 |
| GB | 2 131 701 | A | | 6/1984 | |
| WO | WO-2010127647 | A1 | * | 11/2010 | ............. A61K 31/17 |
| WO | 2013028214 | A1 | | 2/2013 | |

OTHER PUBLICATIONS

Melchore, James A., "Sound Practices for Consistent Human Visual Inspection," AAPS PharmSciTech, vol. 12, No. 1, Mar. 2011, pp. 215-221. (Year: 2011).*

De Moura et al., "Aqueous Extract of Brazilian Green Propolis: Primary Components, Evaluation of Inflammation and Wound Healing by Using Subcutaneous Implanted Sponges," Evidence-Based Complementary and Alternative Medicine, vol. 2011, Article ID 748283, pp. 1-8 (Year: 2011).

* cited by examiner

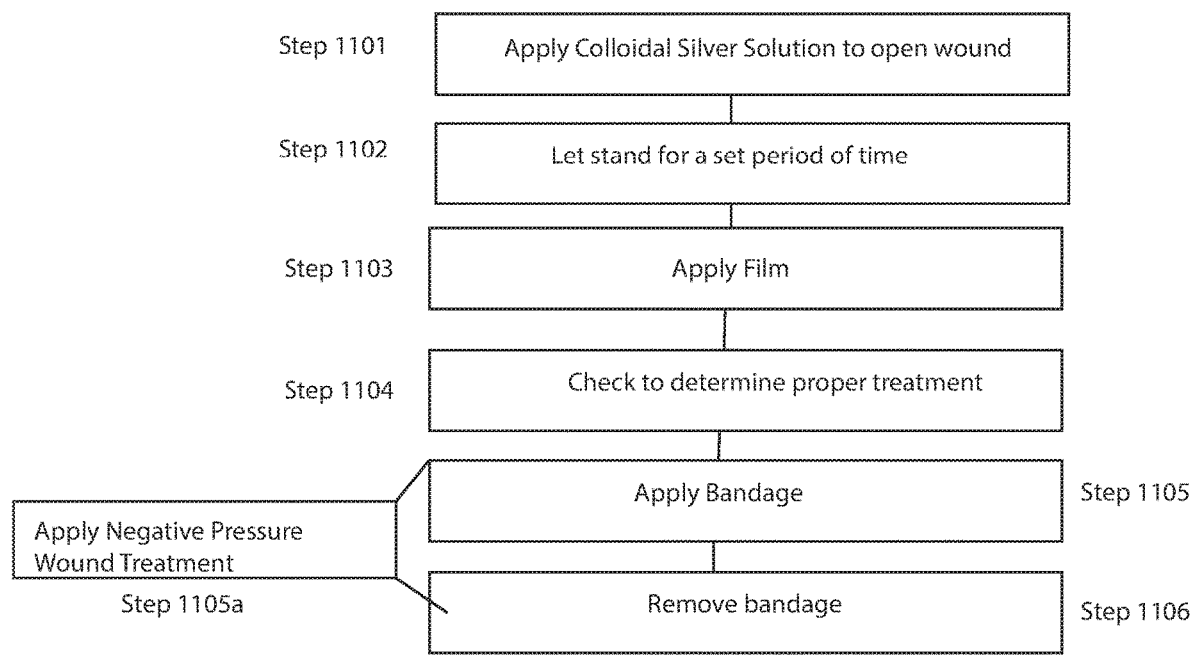

SYSTEM AND METHOD FOR TREATING A WOUND

CROSS REFERENCE TO RELATED APPLICATIONS

This application is a divisional of U.S. application Ser. No. 15/419,965 filed on Jan. 30, 2017 which claims priority from U.S. Provisional Application No. 62/288,612 filed on Jan. 29, 2016 the disclosures of both applications are hereby incorporated by reference in their entirety.

BACKGROUND OF THE INVENTION

In at least one embodiment of the invention, there is a system and method for treating a wound. There are different types of wounds to be treated, for example there are closed wounds, and open wounds. With respect to open wounds there are topical wounds which are relatively superficial and deeper open wounds. With these open wounds they can be in the form of a clean wound which is made under relatively sterile conditions, with relatively no organisms present, a contaminated wound, such as those resulting from accidental injury with pathogenic organisms or foreign bodies in the wound, an infected wound which includes pathogenic organisms which are present and multiplying and which exhibit signs of infection such as yellow appearance, soreness, redness oozing pus, or a colonized wound which is a chronic situation where there are pathogenic organisms and which are difficult to heal such as a bedsore. Since the increasing progression of pathogens inside of a wound can be quite harmful to a patient, there is a need for a solution and a treatment of wounds to prevent the worsening of a condition of any of these types of wounds.

SUMMARY OF THE INVENTION

In at least one embodiment there is a wound application comprising at least one film applied over a wound comprising at least 1% green tea, and at least 0.01% sugar, wherein said film comprises a polymeric film comprising united chains and monomeric glucose points.

In at least one other embodiment of the invention there is a wound application comprising a solution comprising at least trace amounts of colloidal silver, at least trace amounts of sodium chloride, at least trace amounts of dextrose; and water, wherein the colloidal silver, the sodium chloride and the dextrose are dissolved in water.

In at least one embodiment of the invention there is an application for treating a wound comprising both a solution comprising at least trace amounts of colloidal silver and a film comprising at least trace amounts of green tea applied over the solution on top of a wound.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views:

FIG. 11 shows the process for applying the colloidal silver solution with a film and a bandage.

DETAILED DESCRIPTION OF PREFERRED EMBODIMENTS

Figure 1:
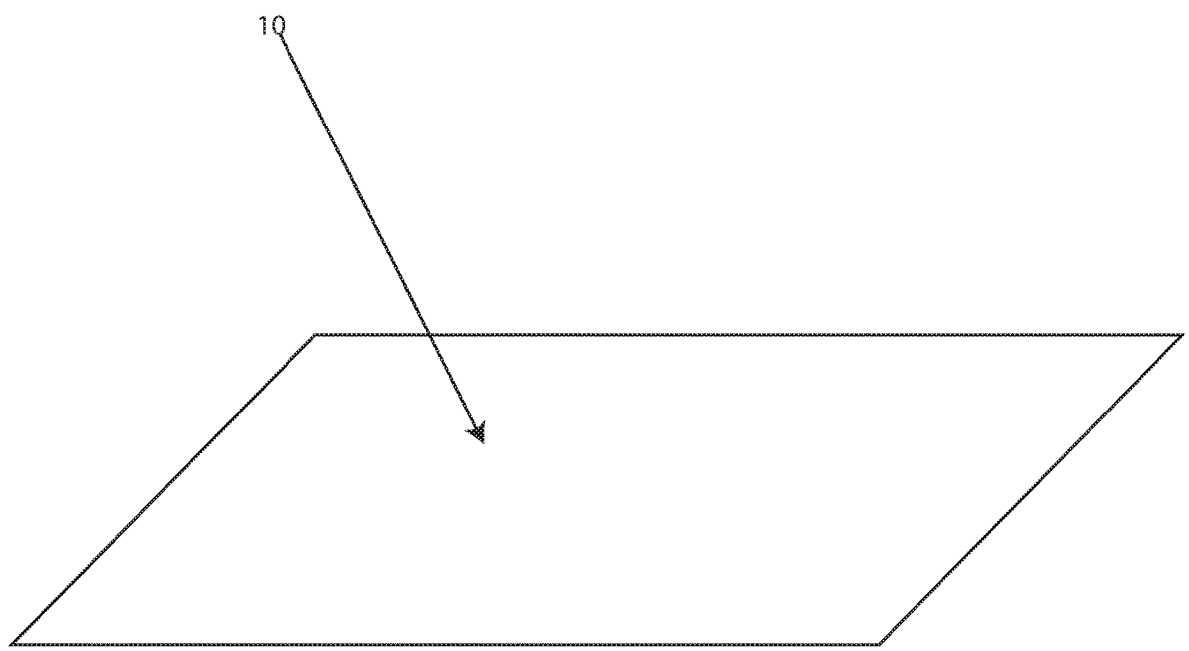
FIG. 1 shows a view of a bandage or dressing for a wound.

Referring to the drawings, FIG. 1 shows an applicator pad 10 for applying over an open or topical wound. The pad can be infused with a type of solution for treatment of a wound. The pad can be placed over a wound, to either lie over a wound, to sit under a wound or to be secured over a wound with either a wrap or an adhesive.

Figure 2:
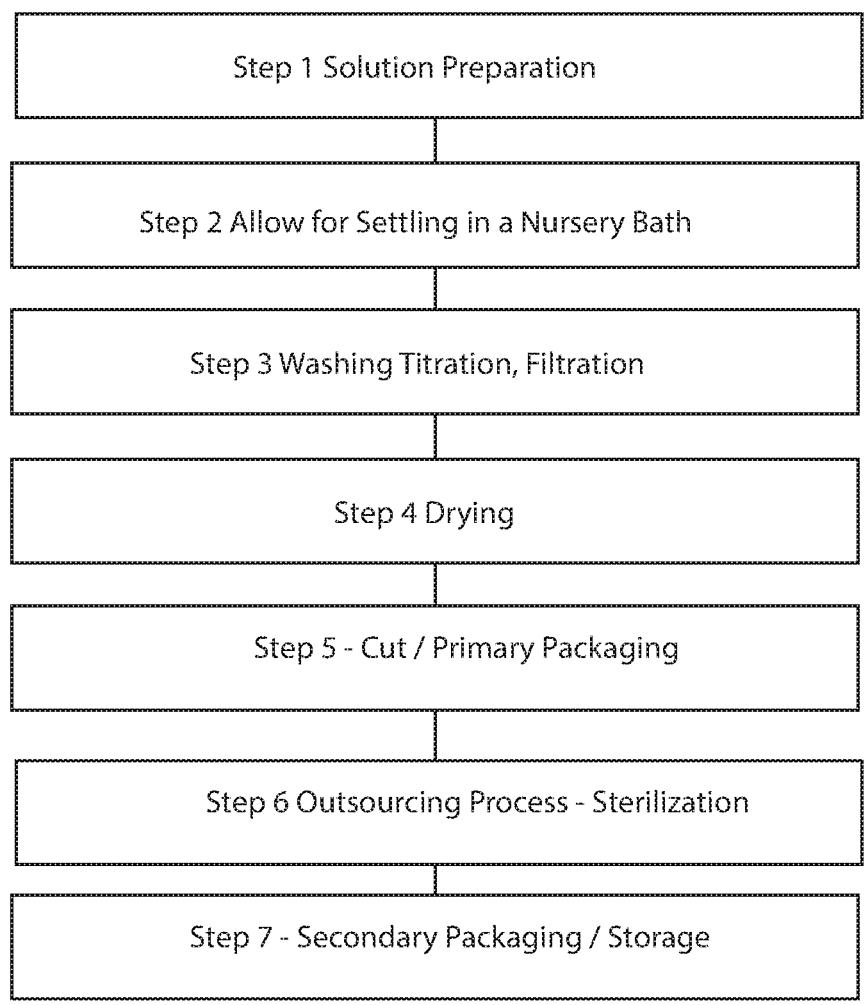
FIG. 2 shows a process for preparing a bandage or dressing for a wound.

FIG. 2 shows a process including a set of general steps for creating a solution for aiding in the treatment and cleansing of a wound. In this process in step 1 there is the basic step of solution preparation which is detailed further in FIG. 3. Next in step 2, the solution is allowed for settling in a nursery bath this is shown in greater detail in FIG. 4. Next, in step 3 the solution is washed, titrated and filtered which is shown in greater detail in FIG. 5. Next, in step 4 the solution is dried which is shown in greater detail in FIG. 6. Next, in step 5 the solution is cut and set forth for primary packaging which is shown in greater detail in FIG. 7. Next, in step 6 the solution is sterilized and outsourced, to a distributor which in step 7 is set out for secondary packaging or storage.

Figure 3:
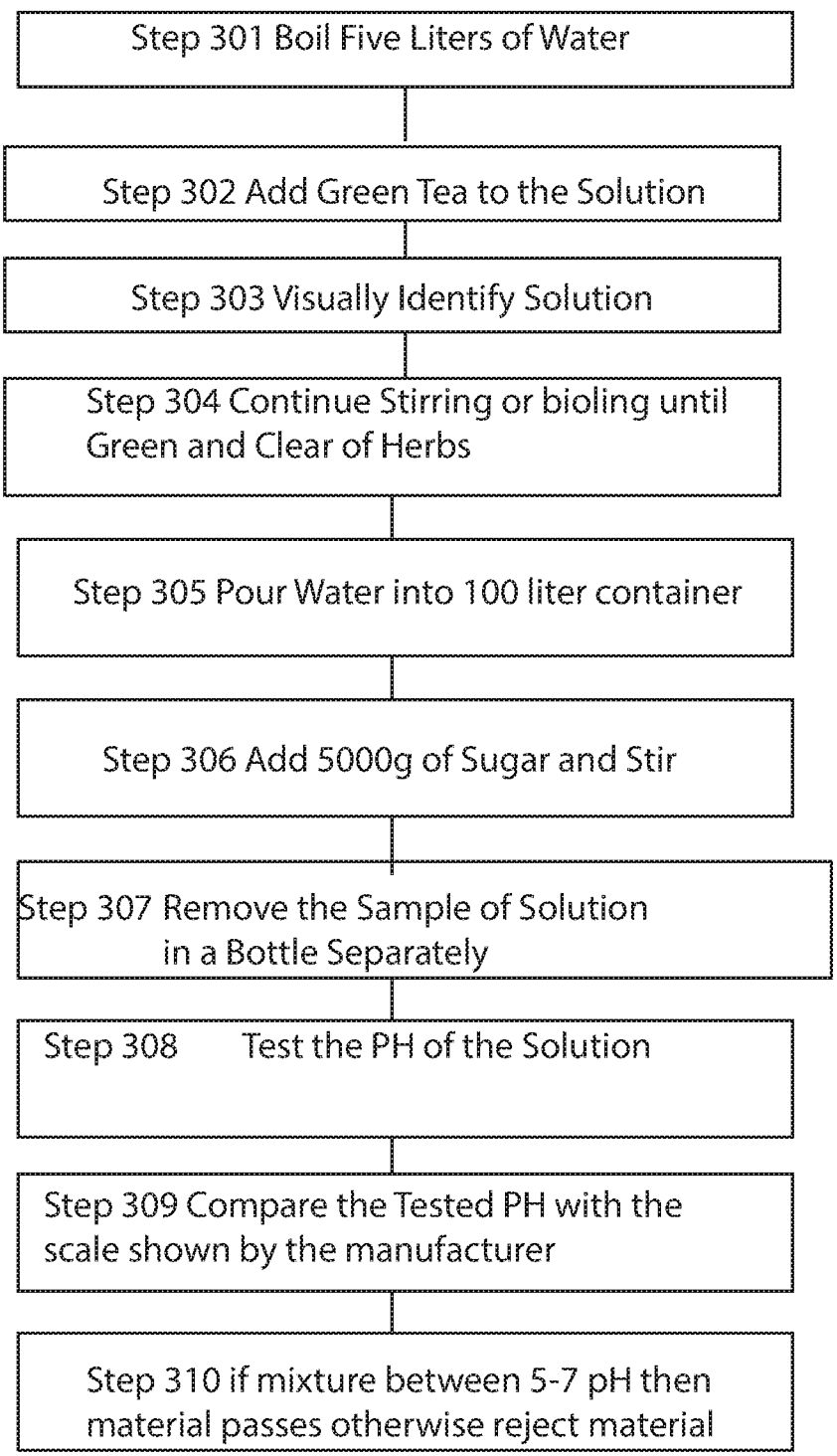
FIG. 3 shows the process for the preparation of the solution for the bandage or dressing.

In FIG. 3 there is a more elaborate process for creating the solution. For example, in FIG. 3 there is step 301 which starts with boiling a pre-set amount of water. In at least one example 5 liters of water can be boned. Next, in step 302 green tea can be added to the solution. The amount of green tea necessary can be determined either visually or based upon a pre-set amount such as 150 grams of green tea. Next, in step 303 the party creating this solution can visually identify this solution. In this step the mixture must show a presence of green color and an absence of solid material such as herbs or precipitate. The frequency of this visual conformation would be on the order of substantially 100% which means anywhere between 95 and 100%. The determination can be made either by a human eye, a machine identifying this feature or a combination of the two. In at least one embodiment, a machine can be in the form of a computer coupled to a camera.

Next, in step 304 the system can continue stirring or boiling until the solution is green and/or clear of herbs. Next, in step 305 the system can pour the solution into a container. In at least one embodiment, the container can be in the form of a 100-liter container. Next in step 306, the user can add 5000 g of sugar to the solution and then stir the solution more. The stirring can be performed by a computerized stirring device which repeatedly stirs the solution. Next, in step 307, the solution can be removed in a bottle separately to test it at a batch level. Next, in step 308, the system can test the pH of the solution by immersing a pH testing strip or tester into the solution for at least 1-3 seconds. Next in step 309 the system can compare the tested pH with a pre-set scale. Next in step 310, the system can confirm whether the pH of the solution is between 5-7 pH and then the material passes the initial test or it is otherwise rejected. At this stage, more of the solution in the original container such as in this example the 100-liter container is mixed further and either more sugar, more water, or more green tea is added to the solution.

Figure 4:
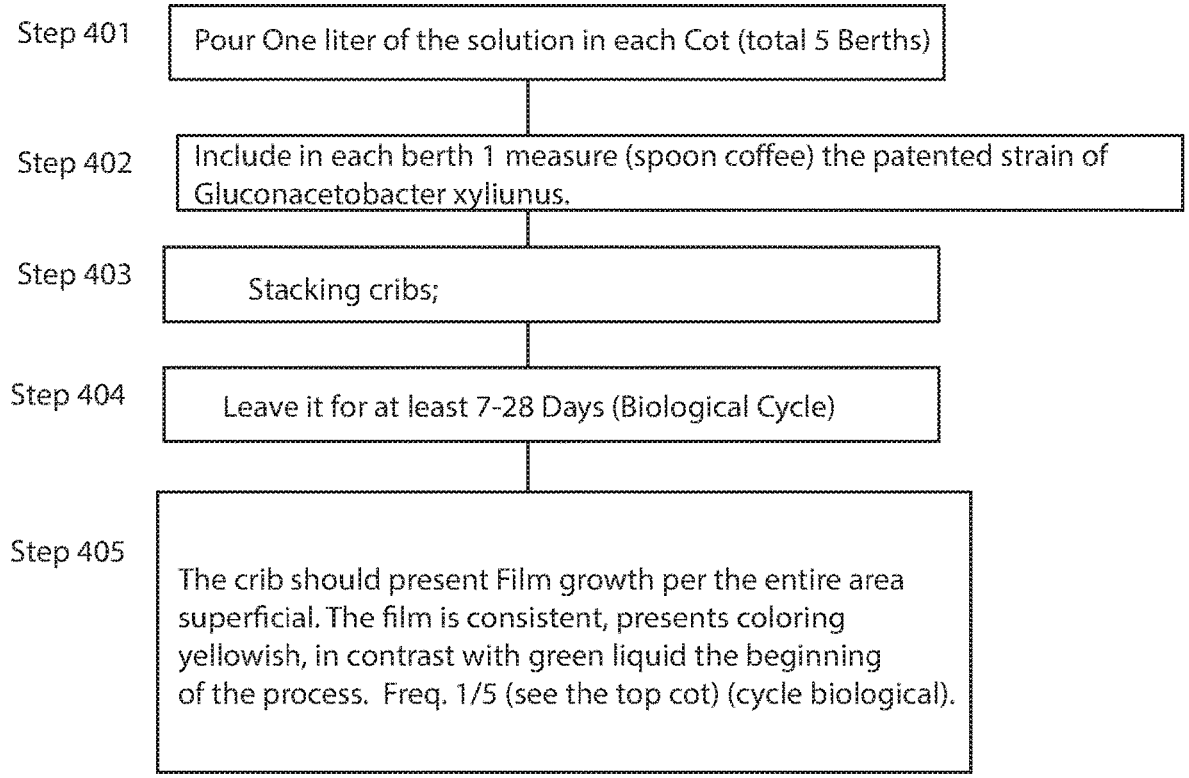
FIG. 4 shows a further step in treatment of the solution.

Provided the solution passes the first test, FIG. 4 starts with step 401 wherein the system can pour one liter of solution into each Cot for a total of five Berths. In at least one embodiment the cot contains an applicator pad such as applicator pad 10. Next, in step 2 the system can include in each berth one measure (spoon coffee) a strain of *Gluconacetobacter xylinus*. Next, in step 403 the system can set the cots into the stacking cribs. Next in step 404 the system can leave these cots for at least 7-28 days (1-4 weeks). In step 405 the crib should be inspected to observe film growth as per the entire area. The film growth should be at least superficial. The film should be persistent, present coloring that is yellowish, in contrast with green liquid at the beginning of the process.

Figure 5:
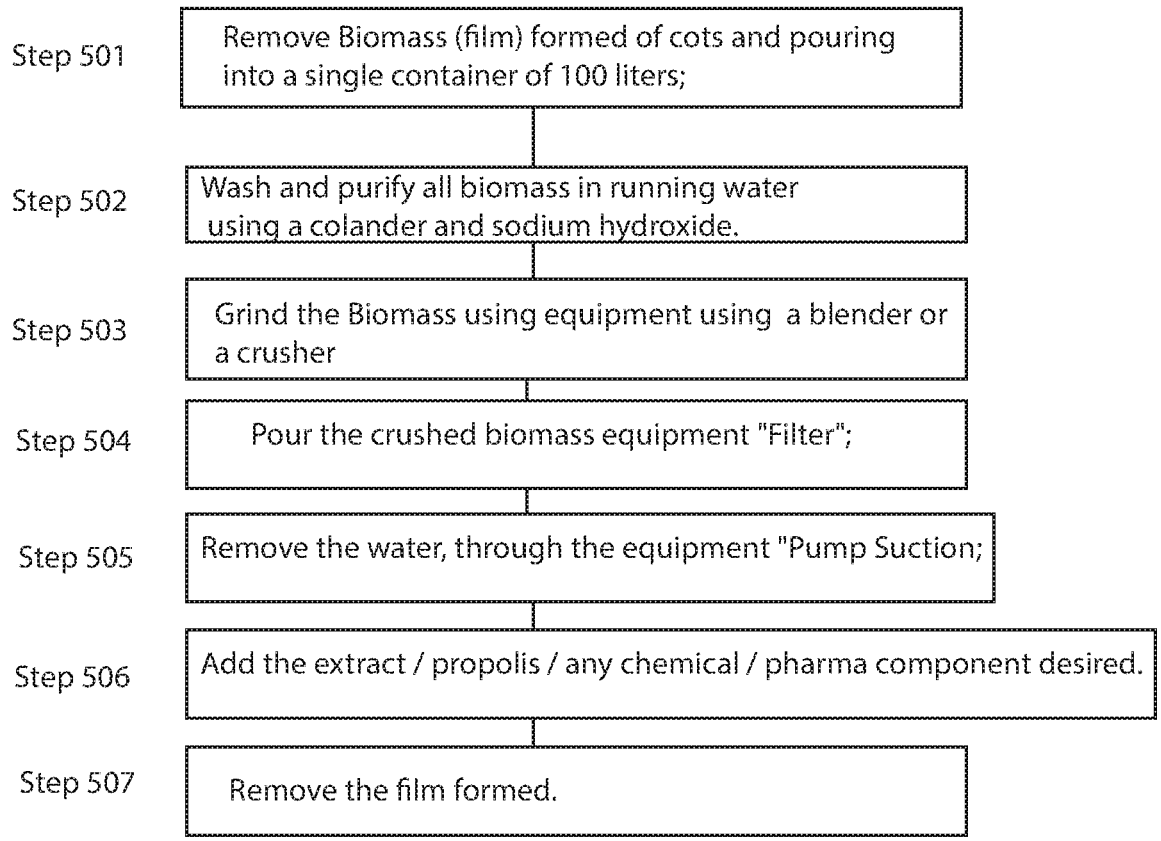
FIG. 5 shows the step in the formation of a film.

FIG. 5 shows the process associated with step 3 in greater detail. In this process it begins with step 501 where the biomass film is removed from the cots and poured into a single container of 100 liters. Next, in step 502 the biomass is washed and purified in running water using a colander and sodium hydroxide. Next, in step 503 the biomass is ground using a crusher or a blender. Next in step 504 the crushed biomass is poured into a filter. Next, in step 505 the excess water is removed. Next, in step 506 an extract such as propolis or any additional chemical or pharmacological component can be added as well. Next, in step 507 the film that was formed is removed.

Figure 6:
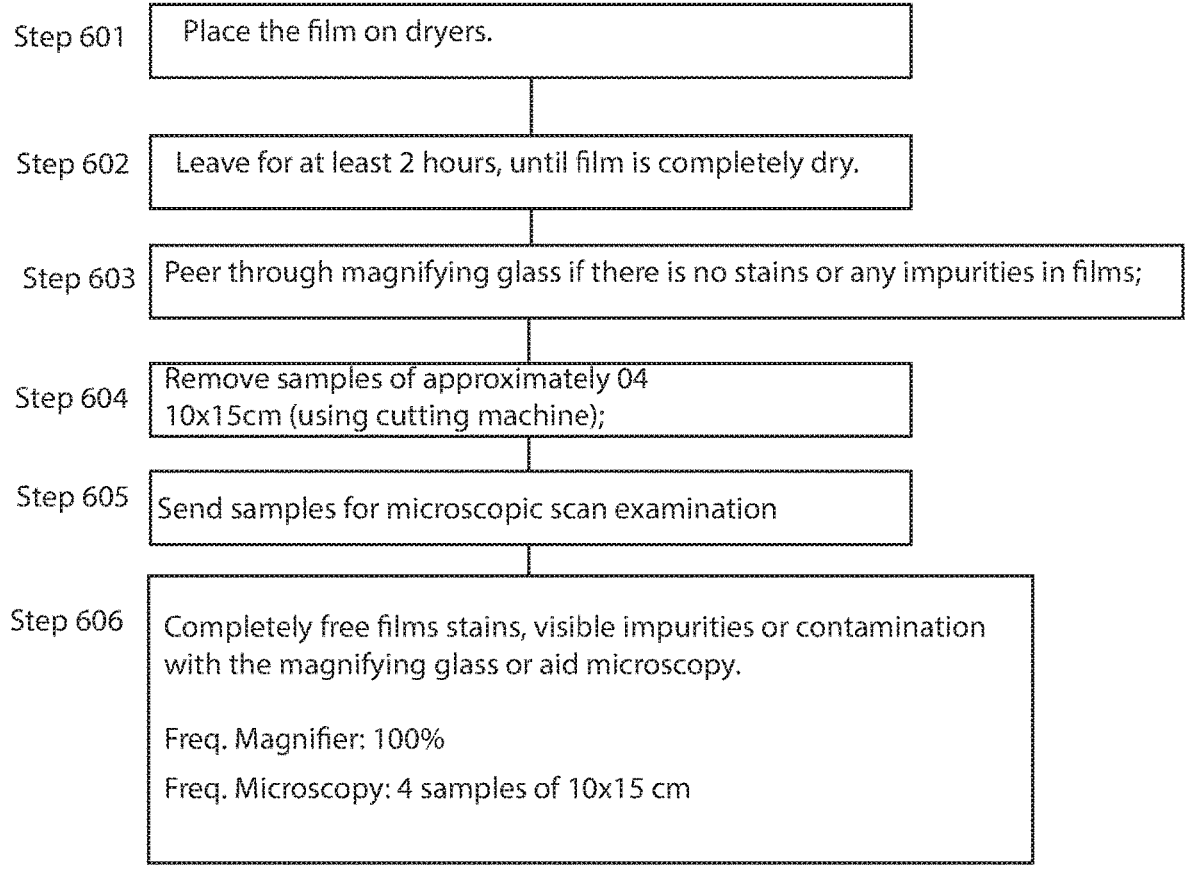
FIG. 6 shows the steps for the drying of the films.

FIG. 6 shows another series of steps that are associated with step 4 which relates to drying of the material. For example, the process starts in step 601, wherein the film is placed on dryers. Next, in step 602 the material can be left for at least 2 hours until the film is completely dry. Next, in step 603 the film can be optically reviewed through a magnifying glass to see if there are any stains or impurities. Next, in step 604 the samples are cut to approximate dimensions of approximately 10×15 cm using a cutting machine. Next in step 605 these samples can be sent to a microscope for further examination. Next, in step 606 the film is reviewed to see whether it is free of films, stains, visible impurities or contamination by viewing under a magnifying glass or via microscopy.

Figure 7:
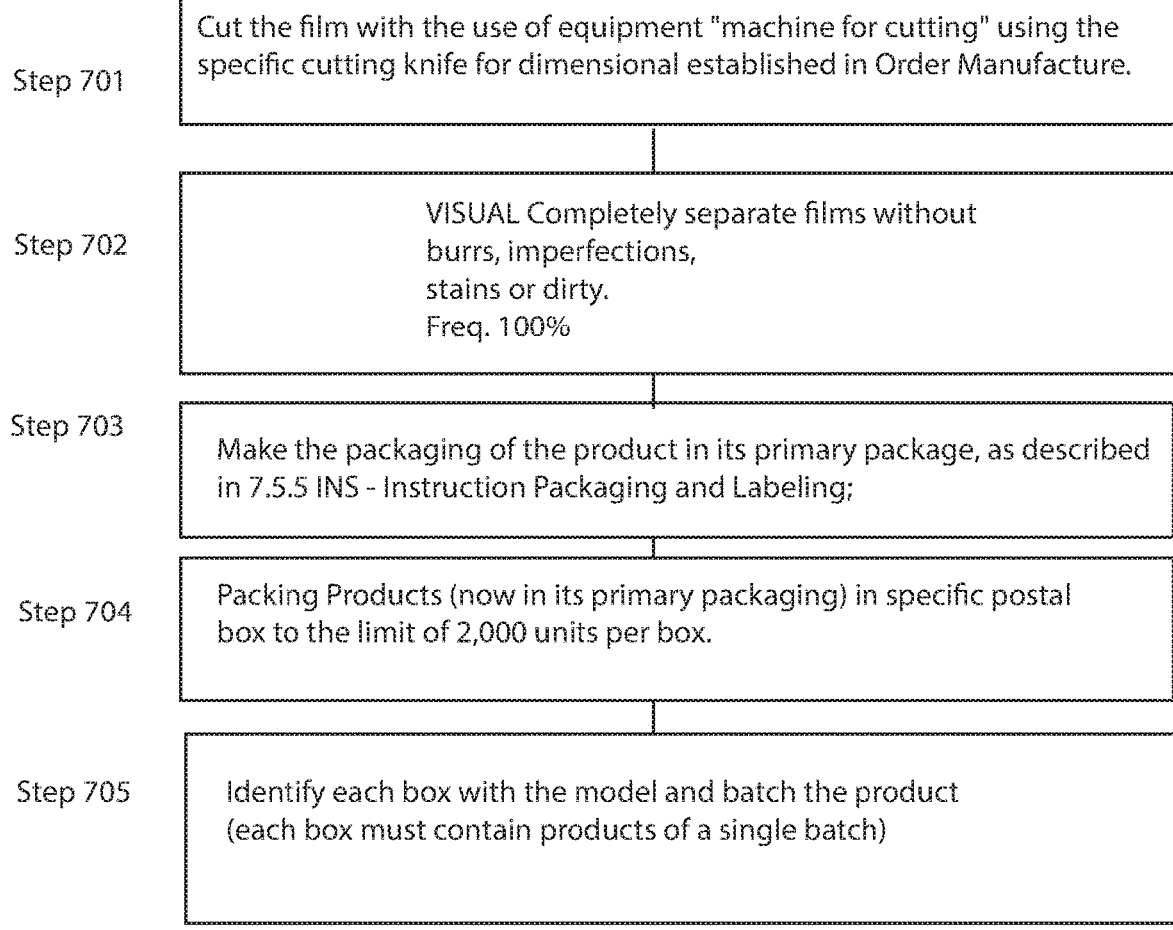
FIG. 7 shows the steps for the packaging of the films.

FIG. 7 shows the flow chart for the process for cutting the dried film. For example, it starts in step 701 wherein the film is cut with the use of a machine for cutting using a cutting knife to cut a pre-dimensioned piece of bandage or covering for a wound. In step 702, each of the products can be visually inspected either by a computer inspector comprising a camera or visually inspected by a person or both. This inspection is to determine if there are any burrs, imperfections, stains or if they are dirty. It is to be used to determine that all or nearly all such as substantially 100% (at least 95-100%) of the films meet these pre-defined criteria.

Next, in step 703 the system can make a packaging of the product in its primary package. Next, in step 704 the system can package the products in a specific postal box up to 2000 units per box. Next in step 705 the system can identify each box with the model and batch of the product such that each box contains the product of a single batch.

Ultimately, the membrane formed by the hemicelluloses polymeric film in a polysaccharide chemical composition is structured by united chains and monomeric glucose points. It configures a hemicellulose constitution with the following characteristics; translucent, thickness, flexibility, and density when re-hydrated in physiological solution. There is low solubility in aqueous medium due to systematic gas exchange and exit of aqueous vapors. It is compatible with human skin and allows the elimination of exudates and tissue oxygenation. It aids in the guided healing of chronic or acute lesions, it also provides considerable pain relief which translates into patient comfort. The contents can include natural cane sugar, baccharis dracunculifolia extract which includes the stem cells of the plant, green propolis from the baccharis dracunculifolia plant, and the bacteria strain of *Gluconacetobacter xylinus* or any strain that produces a fiber size between 2 nm-50 nm.

The membrane is obtained by a natural biotechnological process through biomass production that involves a culture medium where yeast in symbioses develops the product. It is the result of a symbiotic association between yeast and strains of *Gluconacetobacter xylinus*. The extract and propolis components are then added when the biomass has been purified and cleaned, right before drying.

When treating a patient, the film which is formed on the pad can then be applied to a wound to cover the wound. The solution inside of the film can then come into contact with the biological material or body which contacts the film so that the solution or film can act against any infection inside of the wound.

In addition, in at least one additional embodiment, a wound can be treated in another multi stage procedure in which an antiseptic solution comprising at least trace amounts of colloidal silver are sprayed onto an open wound and then the film in the form of the pad infused with the solution made in the steps outlined above, is applied over the wound to further treat the wound.

In at least one embodiment the colloidal silver solution can comprise a water solution comprising 0.003% colloidal silver (30 ppm) 0.01% sodium chloride, and 5% dextrose. This spray system can be effective for applying levels of colloidal silver into a wound bed for cleansing a wound and for providing an antimicrobial effect on the wound bed. In at least one embodiment it has at least 30 ppm colloidal silver. In another embodiment, it has higher quantities such as up to 40 ppm or even 50 ppm colloidal silver. In at least one embodiment it can have lower concentrations of colloidal silver such as at 20 ppm, or even as low as 10 ppm. The solution is relatively colorless and odorless, and in most cases alcohol free resulting in relatively no staining of the wound, and it can be effective within relatively three minutes which provides patients confidence in use. The colloidal silver solution is configured to destroy the host cell membrane and interferes with cellular enzymes by penetrating cell membranes thus preventing bacterial proliferation. Thus, there are examples provided below:

Example 1

| | |
|---|---|
| Green Tea | 150 g |
| Natural Cane Sugar | 5000 g |
| *Gluconacetobacter xylinus* | 5 measure (spoon coffee) |
| Bee Propolis | .01 wt %-10 wt % |
| Water | 100 liters |

The above solution is eventually infused into a bandage or dried separate from a bandage to form a film which is then applied to a wound.

In another example, the following amounts are used:

Example 2

| | |
|---|---|
| Green Tea | 200 g |
| Natural Cane Sugar | 5000 g |
| *Gluconacetobacter xylinus* | 5 measure (spoon coffee) |
| Bee Propolis | .1 wt %-1 wt % |
| Water | 100 liters |

Example 3 is Shown Below

| | |
|---|---|
| Green Tea | 150 g |
| Natural Cane Sugar | 5000 g |
| *Gluconacetobacter xylinus* | 5 measure (spoon coffee) |
| Bee Propolis | .1 wt %-1 wt % |
| Water | 100 liters |

Thus, depending on the proposed components added, these different solutions can be used to form a film either infused into a bandage or separate from a bandage. The film can then be applied to an open wound to treat the wound.

Figure 8:
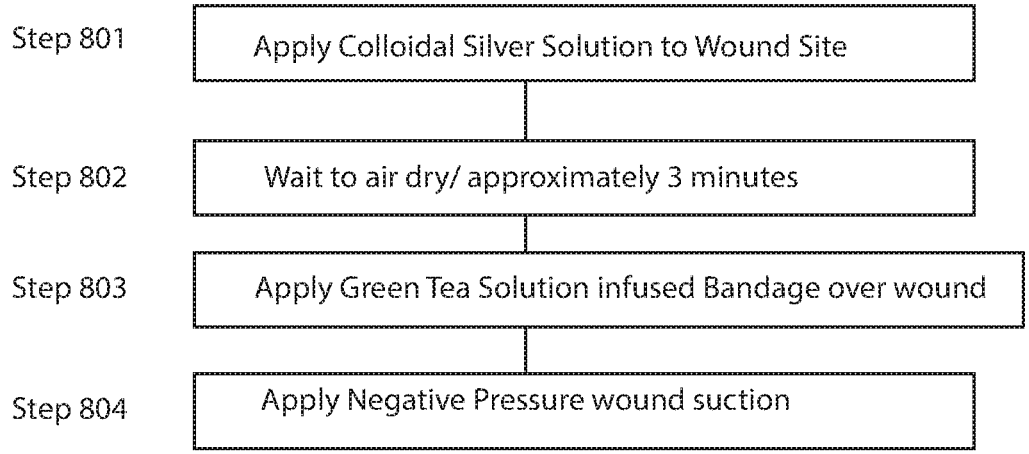
FIG. 8 shows the process for applying two solutions for wound treatment.

Thus, in FIG. 8 there is a process for applying this specific colloidal silver solution outlined above having at least 30 ppm of silver. In this step the application can comprise either spray application, or gel application to the open wound site in step 801. Next in step 802, the applicator such as medical personnel can waft to air dry the solution for approximately 3 minutes. This term of approximately 3 minutes can range between 2.5 minutes and up to 4 minutes. Next, in step 803, the medical professional can apply the film infused bandage over the wound. This film infused bandage comprises the solution prepared as outlined in the steps shown in FIG. 2. Next, in step 804 the medical professional can, as needed, apply a negative pressure wound suction to draw fluids out of the wound to prevent any further infection and to promote a faster healing of the wound.

Alternatively, the colloidal silver solution can be applied separately to open wounds without the use of the covering of the film comprising at least partially of green tea. For example, a colloidal silver solution can be formed as either a component of a gel or a spray. For example, if the colloidal silver solution is used with a spray the colloidal silver component can be added to water such as distilled water. Next, 0.01% sodium chloride is added to the solution. In addition, 5% wt. % of dextrose is also added to the solution. This solution is thoroughly mixed so that it forms a substantially uniform spray.

Alternatively, if these components are added to a gel for application to an open wound, the colloid silver solution at 30 ppm, the Sodium Chloride at 0.01% (wt. %), and the Dextrose at 5% (wt. %) are added to a gel and then thoroughly mixed and infused into the gel. In at least one embodiment, the gel is in the form of a hydrogel, however as suitable other gels can be used. For example, one example of the solution is shown below:

Example 4

| | |
|---|---|
| Colloid Silver | .003% (wt. %) approximately 30 ppm |
| Sodium Chloride | 0.01% (wt. %) |
| Dextrose | 5% (wt. %) |
| Water | Remainder of solution (approximately 94.987% wt. %) |

Example 5

| | |
|---|---|
| Colloid Silver | .004% (wt. %) approximately 40 ppm |
| Sodium Chloride | 0.01% (wt. %) |
| Dextrose | 5% (wt. %) |
| Water | Remainder of solution (approximately 94.986% wt. %) |

Example 6

| | |
|---|---|
| Colloid Silver | .005% (wt. %) approximately 50 ppm |
| Sodium Chloride | 0.01% (wt. %) |
| Dextrose | 5% (wt. %) |
| Water | Remainder of solution (approximately 94.985% wt. %) |

Example 7

| | |
|---|---|
| Colloid Silver | .003% (wt. %) approximately 30 ppm |
| Sodium Chloride | 0.01% (wt. %) |
| Dextrose | 5% (wt. %) |
| Gel | Remainder of solution (approximately 94.987% wt. %) |

Example 8

| | |
|---|---|
| Colloid Silver | .004% (wt. %) approximately 40 ppm |
| Sodium Chloride | 0.01% (wt. %) |
| Dextrose | 5% (wt. %) |
| Gel | Remainder of solution (approximately 94.986% wt. %) |

Example 9

| | |
|---|---|
| Colloid Silver | .005% (wt. %) approximately 50 ppm |
| Sodium Chloride | 0.01% (wt. %) |
| Dextrose | 5% (wt. %) |
| Gel | Remainder of solution (approximately 94.985% wt. %) |

Depending on the need for treatment and the type of wound, different amounts of colloidal silver can be used and with different types of applicators such as via a spray from a spray bottle or via a gel placed on the open wound site.

As indicated above by the different examples, the colloidal silver amounts can be varied based upon the type of the open wound and the apparent amount of contamination.

The application either via a gel or a spray works to actively attack and kill bacteria and other microbial proliferation to sterilize and sanitize a wound.

Figure 9:
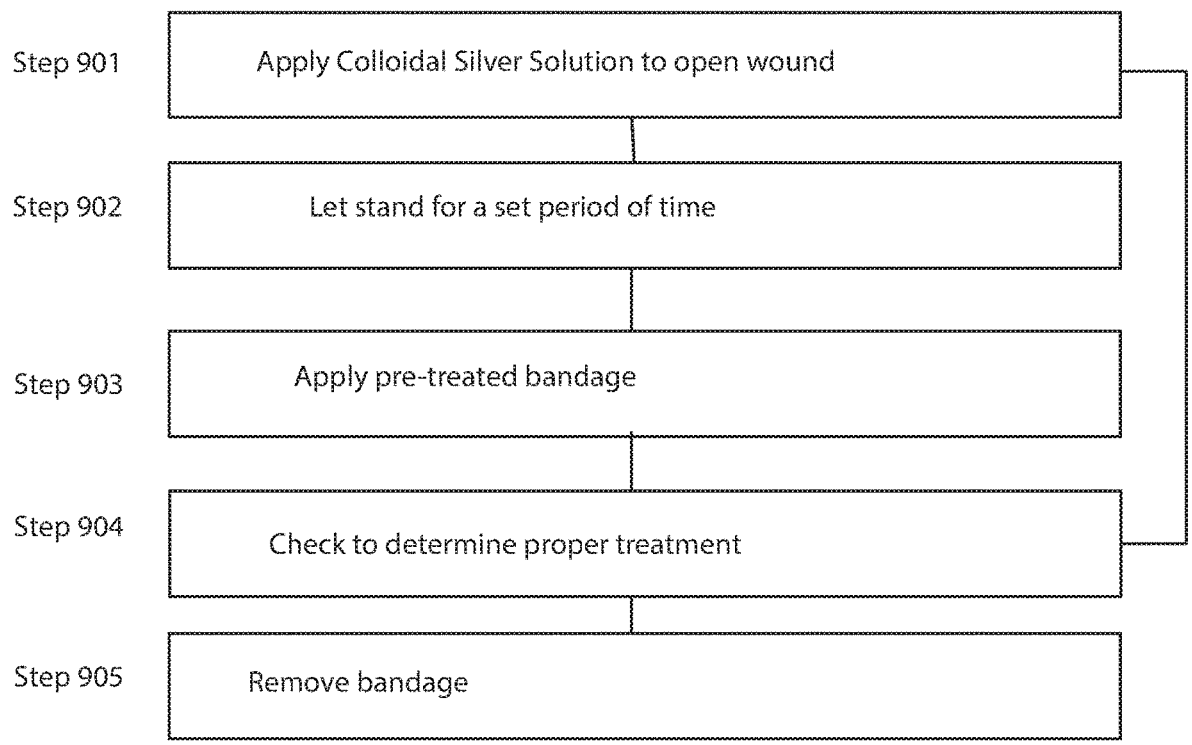
FIG. 9 shows the process for applying the colloidal silver solution.

FIG. 9 shows the flow chart for applying colloidal silver solution with a bandage. For example, the process starts in step 901 wherein the colloidal silver solution of any one of the above examples is applied either as a spray on solution or as a gel. Next, in step 902, this solution is allowed to let stand on the wound for a pre-set period of time for examination. In at least one embodiment, the pre-set period of time is at least three minutes. Next, the medical practitioner can apply a bandage in step 903. Next, in step 904, the medical practitioner can check to determine if this administration of this colloidal silver solution was properly applied and properly healed the wound. Next in step 905, the user could remove the bandage and let the healed wound remain open to the aft.

Figure 10:
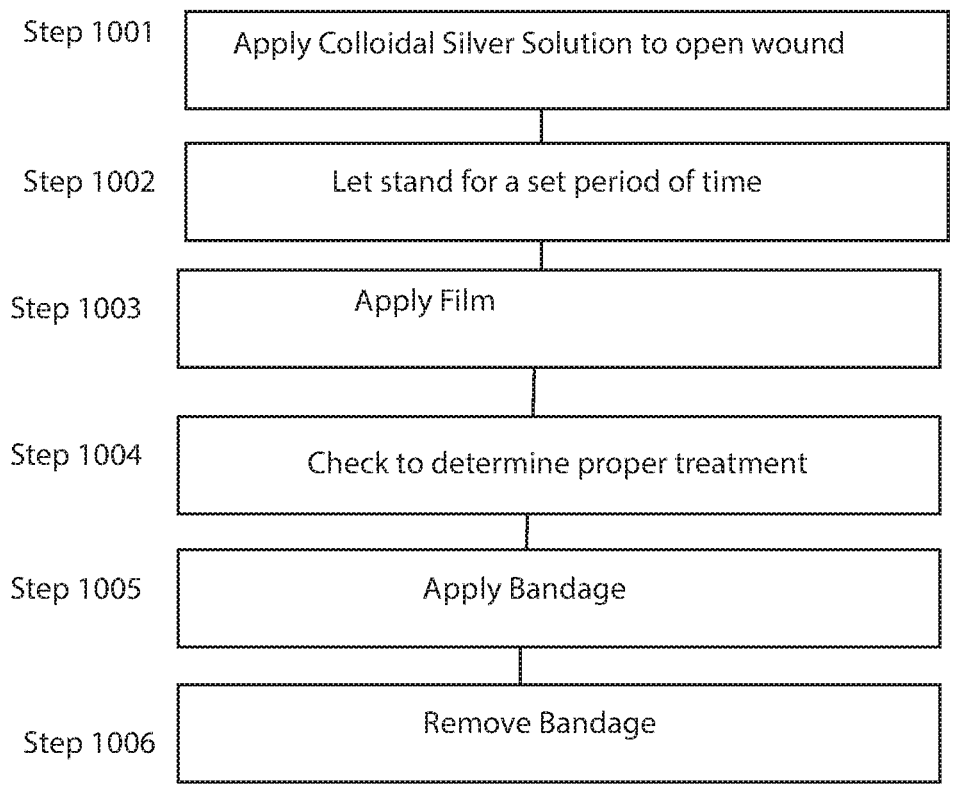
FIG. 10 shows the process for applying the colloidal silver solution with a film.

FIG. 10 shows a flow chart for another application to treat a wound which comprises step 1001 which includes applying a colloidal silver solution to an open wound. Next, in step 1002, the medical practitioner can allow the colloidal silver solution stand for a predetermined period of time. In at least one embodiment, the predetermined period of time can be at least three minutes. Next, in step 1003, the practitioner, can apply a film such as the film disclosed above comprising at least trace amounts of green tea. Next, after the film is allowed to stand over the open wound, the medical practitioner can examine the wound, to determine if there is a proper application. Next, in step 1005, the practitioner can apply a bandage. Next in step 1006 the practitioner can remove the bandage when the wound has healed.

Another embodiment for the treatment of a wound is shown in FIG. 11. In this embodiment, the process starts in step 1101 wherein the medical practitioner can apply a colloidal silver solution to an open wound. This application can be in the form of a spray application or in the form of a gel application. Next in step 1102, the practitioner can allow this application to stand for a pre-set period of time such as for at least three minutes. Next, in step 1103, the practitioner can apply a film to the open wound. The film can be any one of the type disclosed above in examples 1-2. Next, in step 1104, the practitioner can check the wound to determine the proper pre-treatment of the wound. Next, in step 1105, the practitioner can apply a bandage. Once the bandage is applied, the user can optionally apply a negative pressure wound treatment to the open wound. This negative pressure wound treatment can be used to draw biologics and fluid out from the wound. Next, once the wound has healed, the practitioner can remove the bandage in step 1106.

As indicated above, the green tea infused film can be used for the purpose of covering and protect sutures and lesions, with or without exudates, in unfavorable healing situations. This green tea solution is adequate for use in several parts of the body for patients of all ages. It can be used for the treatment of first and second degree burns, for the treatment of wounds with loss of skin, with or without bleeding, for the treatment of chronic ulcers that present with hard tendency to healing with the use of conventional dressings, for the treatment of ulcers and treatment of diabetic patients. The green tea solution with or without a bandage application can be used as a temporary human skin substitute, acting as a mechanical barrier allowing wound healing.

Accordingly, while at least one embodiment of the present invention have been shown and described, it is to be understood that many changes and modifications may be made thereunto without departing from the spirit and scope of the invention as defined in the appended claims.

What is claimed is:

1. A process for treating a wound comprising:
preparing a solution comprising the steps of:
   boiling water;
   applying green tea leaves;
   adding sugar;
   testing a pH of the solution to determine whether the pH is between 5-7;
   modifying the pH of the solution to make it within the pH of between 5-7 if the solution is outside of the range of a pH of 5-7;
   adding *Gluconacetobacter xylinus;*
   placing the solution into separate containers;
   allowing the solution to sit for a predetermined time of at least 7 days;
   settling the solution;
   inspecting the solution to determine whether the film changes color from green to yellow, to determine film growth before removing the film from its container;
   washing the solution using sodium hydroxide;
   drying the solution to form a film;
   reviewing the film under magnification;
   cutting the film to fit a bandage;
   packaging the film for use in treatment wherein the film comprises at least 1 wt % green tea and at least trace amounts of sugar;
   applying colloidal silver in a form of a spray to a wound site before applying the film such that the treatment includes at least 30 ppm colloidal silver;
   applying the film to a pad and then applying the pad to the wound site; and
   applying a negative pressure to the wound site to draw fluids out of the wound.

2. The process as in claim 1, further comprising the step of visually reviewing the solution to determine the color of the solution to determine whether the solution has settled.

3. The process as in claim 2, further comprising the step of allowing the solution to cure to form a biomass and then removing the biomass from the separate containers and placing the biomass into a single container.

4. The process as in claim 3, further comprising the step of purifying the biomass using water, a colander and sodium hydroxide.

5. The process as in claim 4, further comprising the step of grinding the biomass.

6. The process as in claim 5, further comprising the step of pouring the crushed biomass through a filter.

7. The process as in claim 6, further comprising the step of removing water from the biomass.

8. The process as in claim 7, further comprising the step of removing any film formed on the biomass.

9. The process as in claim 1, further comprising the step of applying the colloidal silver in the form of a gel after applying the colloidal silver in the form of a spray.

10. The process as in claim 1, further comprising the step of applying the colloidal silver in the form of a spray and further comprising providing at least one of sodium chloride, dextrose and water.

11. The process as in claim 1, wherein the step of adding sugar comprises adding 50 grams of sugar per liter of water of the solution.

* * * * *